United States Patent [19]
Driskell et al.

[11] 3,950,850
[45] Apr. 20, 1976

[54] DENTAL PROSTHETIC IMPLANTS

[75] Inventors: Thomas D. Driskell; Alfred L. Heller, both of Worthington; Joseph F. Koenigs, Columbus, all of Ohio

[73] Assignee: Miter, Inc., Worthington, Ohio

[22] Filed: Feb. 25, 1974

[21] Appl. No.: 445,567

[52] U.S. Cl. ............................................. 32/10 A
[51] Int. Cl.² ........................................ A61C 13/00
[58] Field of Search .................... 32/10 A; 128/92 R

[56] References Cited
UNITED STATES PATENTS

| | | | |
|---|---|---|---|
| 3,314,420 | 4/1967 | Smith et al. ....................... | 128/92 R |
| 3,465,441 | 9/1969 | Linkow .............................. | 32/10 A |
| 3,499,222 | 3/1970 | Linkow et al. ..................... | 32/10 A |
| 3,797,113 | 3/1974 | Brainin .............................. | 32/10 A |
| 3,849,887 | 11/1974 | Brainin .............................. | 32/10 A |

FOREIGN PATENTS OR APPLICATIONS

| | | | |
|---|---|---|---|
| 1,083,769 | 9/1967 | United Kingdom .............. | 128/92 R |
| 2,096,895 | 3/1972 | France | |

*Primary Examiner*—Robert Peshock
*Attorney, Agent, or Firm*—Frank H. Foster

[57] ABSTRACT

A prosthetic dental implant which is surgically implantable in the maxillary and mandibular alveolar bones, providing a support base with a protruding post to which one or more prosthetic crown replacements are to be mounted. The implant is a high purity, high density, low porosity unitary alumina body having a serrated base. Its integral top is formed to provide an upwardly extending post with a truncated ellipsodially conical configuration for the attachment of a prosthetic tooth crown. The serrated side walls of the base are formed with outwardly projecting protrusions. These protrusions have a serrated or saw toothed cross sectional configuration with alternating horizontal surfaces and downwardly and outwardly tapering oblique surfaces.

18 Claims, 5 Drawing Figures

DENTAL PROSTHETIC IMPLANTS

BACKGROUND

This invention relates generally to dental prostheses and more particularly relates to the replacement of teeth using a biologically compatible, non-resorbable, endostial implant.

The loss of one or more teeth by disease or trauma results in many undesirable consequences. Mastication becomes more difficult and less efficient. Susceptibility to other disease may be increased and, with the passage of time, migration of the teeth may cause complications including malocclusion.

One of the most common techniques for prosthetic restoration involves the use of a partial denture which may be a tooth-borne, tooth and mucosal-borne, or mucosal-borne prosthesis.

Such prostheses however, have several disadvantages. Because relatively high loads are exerted upon these devices, they tend to move or flex, expecially when dependent upon the soft mucosal tissue for support. They may in fact cause a change in contour with substantial loss of the underlying supporting tissue. Furthermore, reshaping of healthy teeth to permit the attachment of the partial denture by means of a clasp, or any of a number of other intracoronal or extracoronal attachments, is often required.

One of the primary disadvantages of partial dentures is the fact that the partial denture receives marginal load support from the underlying alveolar bone at the vacant tooth site or sites, thus forcing the transfer of abnormal lateral stresses to abutting teeth with destruction of peridontal tissues.

Attempts have been made to implant relatively rigid structures within or upon the alveolar bone in a region of one or several contiguous vacant tooth sites. For example, others have implanted a relatively flat, metallic, endosseous blade formed with a plurality of holes or vents. The vents are intended to permit bone to grow through the lock and implant in place. Such metallic blades, known as Linkow vent blade implants, are formed with a truncated, pyramidal or conically shaped flat mounting post which is undercut, where it is attached to the blade portion of the implant. The metallic blades, however, have met with very limited success as a high rate of failure has been experienced.

Implants of carbon have also been attempted, but it has been found that with metallic, and to a lesser extent with carbon, implants the body typically tends to wall off the implant by soft tissue encapsulation which grows as a protective interface between the alveolar bone and the implant. This is a typical host rejection phenomenon. The implant becomes liable to movement, eventually loosens and is lost.

Still others have searched for porous materials believing porosity to be important. The supposition is that the bone tissue or other tissue will grow firmly into the pores of the implant to provide rigid support. Although this has been a very popular approach, to date the efficacy of this concept in practice is relatively poor.

According to the discovery of the present invention a prosthetic implant is disclosed which rigidly and durably supports one or more prosthetic crowns, or other prosthesis amenable to construction upon the implant or implants placed within the alveolar bone.

SUMMARY OF THE INVENTION

The invention is a dental prosthetic, endostial implant comprising (a) a base formed of a relatively high purity, high density and low porosity alumina,, said base having side walls integrally formed with generally horizontally outwardly projecting protrusions and (b) a post extending from said base and contoured in a generally rounded horizontal cross sectional configuration for attachment of at least one prosthetic crown.

The primary object of the invention is to provide a biologically compatible and non-resorbable implant against which alveolar bone will intimately grow to provide a direct mechanical bone to implant interface, permitting the implant to have a high vertical and lateral masticatory load bearing capability.

Another object of the invention is to provide an implant post which is smoothly contoured with rounded surfaces which permit surrounding soft mucosal tissue to constrict snugly at the gingival margin.

Another object of the invention is to provide a prosthetic implant of high strength which is designed to interface with alveolar bone in a manner which maximizes the stress bearing area of the bone to implant interface to permit lateral and vertical forces to be efficiently transferred to the bone.

Another object of the invention is to provide a single tooth implant prothesis constructed in a plurality of alternatively selectable angular relationships between the root base and the post. This plurality of preformed implants gives single unit construction which is contemplated to be advantageous for superior structural strength, with elimination of any split surfaces, introduction of any less compatible bonding materials or possible harbors for microrganisms.

It is a further object of the invention to provide an implant which is elongated or otherwise modified for use in the prosthetic replacement of a plurality of adjacent teeth.

Further objects and features of the invention will be apparent from the following specifications and claims when considered in connection with accompanying drawings illustrating the preferred embodiments of the invention.

Figure 1:
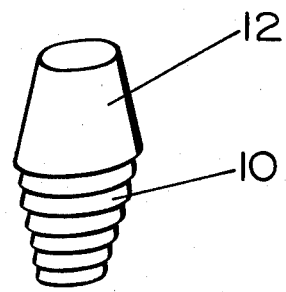
FIG. 1 is a view in perspective of a single tooth root implant embodying the present invention.

In describing the preferred embodiments of the invention illustrated in the drawings, specific terminology will be resorted to for the sake of clarity. However, it is not intended to be limited to the specific terms so selected, and it is to be understood that each specific term includes all technical equivalents which operate in a similar manner to accomplish a similar purpose.

DETAILED DESCRIPTION

Referring now to FIG. 1, a single tooth, endostial implant embodying the present invention is illustrated. The implant is a unitary body having a base 10 preferably shaped generally like a truncated ellipsoidal cone. Its top is formed to provide a post 12 extending from the base for attachment of an artificial tooth crown. Such crowns are commonly known in the art and may be easily adapted for attachment with cement or other medium to the post 12.

Preferably the attachments or mounting post in all embodiments of the invention is smoothly contoured or generally rounded in the horizontal cross sectional plane in order to permit the soft mucosal tissue to constrict snugly around the post at the gingival margin. The term smoothly contoured is used to describe rounded surfaces as opposed to sharp edges or sharp intersections of surfaces. Most preferably the post is formed in a truncated, ellipsoidally conical configuration.

The side walls of the base are formed with horizontally outwardly projecting protrusions. In the regions where the protrusion surfaces intersect the inner surface of the base, sharp angles are avoided to reduce stress concentration in the ceramic structure.

Preferably, the protrusions comprise a plurality of circumferentially extending, continuous horizontal ridges 14 formed on the side walls of the implant. These ridges 14 have a saw tooth or serrated cross sectional configuration with alternating horizontal surfaces and oblique surfaces which taper outwardly away from the post in order to provide a mechanically effective interlock with the alveolar bone. Such an interlock has been found to sustain the functionally encountered lateral and shear forces. Of particular importance are the horizontal surfaces which effectively transfer the shear forces of mastication to the alveolar bone.

Figure 2:
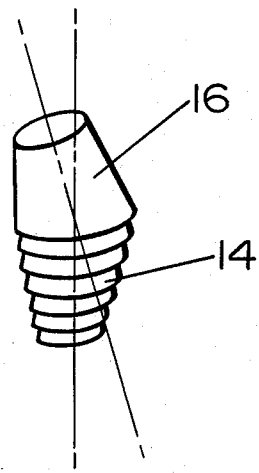
FIG. 2 is a view in perspective of a single tooth root implant having an acutely offset angular intersection between the axis of the implant base and the axis of the attachment post.

FIG. 2 illustrates a single tooth implant similar to the implant illustrated in FIG. 1 but formed so that there is an angle between the longitudinal axis of its base 14 and its post 16. The invention contemplates that a dentist will have access to an inventory of such implants with a variety of different angular orientations being available. For example, implants might be manufactured at 2° intervals from 0° to 16° of intersection angle. The dentist may therefore choose the implant having the crown-root angulation which is appropriate for a particular implant site.

Figure 3:
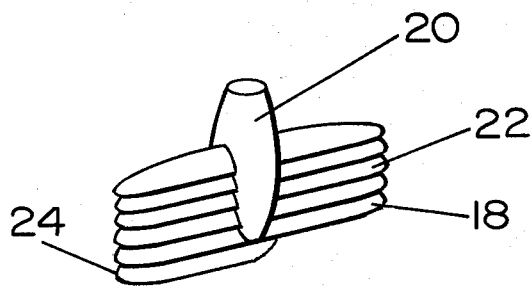
FIG. 3 is a view in perspective of a multi-tooth, dental prosthetic implant embodying the present invention.

FIG. 3 illustrates a relatively more greatly elongated base member 18 formed on the top with a post 20 on which a single or multiple crown prosthesis may be mounted. This relatively long and narrow, endostial blade-type implant provides a suitable base to which prosthetic crown replacements may be attached. The protrusions 22 formed on this blade type implant are preferably conceptually the same as those of the single tooth implant described above.

The post 20 of the implant illustrated in FIG. 3 is molded so that it extends continuously to blend smoothly into the base 18 of the implant. This is an alternative which may be used to improve the stress distribution characteristics of the implant.

The height of the base of implants embodying the present invention is a manufacturing variable dependent upon the dimensions of the bone into which they are to be implanted.

As an additional alternative it is advantageous that some implants be formed with a base having additional height on one side of the post 20 but not on the other. For example, FIG. 3 illustrates an additional protrusion or ridge 24 formed on the implant. The unextended portion of the implant base may be implanted close to the region of a sinus where less bone depth is available while the extended portion provides added bone to implant interface farther from the sinus where more bone depth is available.

Figure 4:
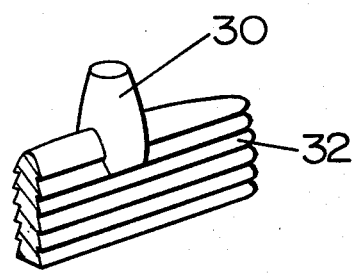
FIG. 4 is a view in perspective with a part broken away to reveal the cross sectional configuration of an alternative embodiment of a multi-tooth implant of the type similar to the implant illustrated in FIG. 2.

FIG. 4 illustrates an alternatively molded post 30 which extends past only one protrusion of the base 32. Additionally, FIG. 4 also illustrates in cross section the preferred serrated or saw tooth configuration of the protrusions extending from the base 32.

The preferred single tooth implant has its post and base shaped generally like oppositely tapering truncated ellipsoidal cones. However, while the multi-tooth implant has a similarly tapering post 20 or 30 shaped like a truncated ellipsoidal cone, its base is preferably not so shaped. Although the base could be so tapered, it is preferably shaped more like an elongated cylinder, with generally parallel sides and rounded ends.

The implants are made of molded and sintered, high density ceramic alumina, $Al_2O_3$ with the post and the base preferably integrally formed into a unitary body. However, the post could be a metal pin seated snugly in a mating opening in the base.

The alumina is a relatively high density and low porosity material, preferably above 93% of the theoretical maximum density. It is also an alumina of high purity, preferably at least 99% pure. We have discovered that breakdown and resorption of the ceramic within the expected lifetime of the implant, is so insignificant with $Al_2O_3$ of 93% density or greater that for practical purposes they do not occur. At lower densities breakdown and resorption do occur.

It has also been found advantageous in some instances, to mix trace quantities of magnesia, silica, calcia, or combinations of these in the alumina. These trace materials improve the strength of the implant, help prevent grain growth and provide a higher density material. They furthermore permit sintering of the alumina at lower temperatures.

Implants embodying the present invention may be used in any mandibular or maxilar position provided that enough bone support is available. Since they are not shaped like a natural tooth they require that appropriate sockets be surgically created to receive them. Although a socket could be formed immediately after the extraction of a natural tooth, such a socket is apt to have undesirable voids around the implant. It is preferred that the socket of a fresh extraction site be permitted to heal and fill with alveolar bone. This permits the implant site to be subsequently shaped exactly as desired.

When the dentist concludes that a tooth can not be saved, the natural tooth is extracted, and normal healing is allowed to take place for 6 to 8 weeks.

Diagnostic models and radiographs are used when planning the size and positioning of the implant site to be created. The dentist must consider the location of the mandibular canal, maxillary sinus and other structures in the immediate area. An implant is then chosen which appears appropriate for positioning in the desired site, taking into consideration the crown-root angulation. If the single tooth implant is used, a surgical opening is made with a round bur through the mucosa and into the newly formed bone, to create a socket. The implant is placed into the socket in close apposition with the bone. It is necessary that there is no vertical movement of the implant after positioning and desirable that no lateral movement be present. Interocclusal distances must be considered to allow for future placement of a prosthetic crown.

With a blade type implant a suitable socket is prepared by making an incision with a scalpel through the mucosa along the alveolar crest to expose the underlying bone. The mucoperiostium is reflected to either side of the ridge. With a surgical bur in a high speed hand piece an elongated groove-shaped socket is formed in a near vertical plane of the mandible or maxilla at the greater height of the ridge. The site is shaped to accept the implant and should be sufficiently deep so that the implant can be positioned two millimeters below the crest of the remaining angular ring with only the post above this ridge. The width and depth of the site will correspond approximately to the dimensions of the implant base. The ridges of the protrusions will extend toward the alveolar bone.

Interocclusal distances must be considered to allow for future placement of a prosthetic crown or bridge.

After the site is created, the implant is inserted into the socket and may be conservatively tapped to implant it within the bone. The surgical site is then closed by suturing the mucosa in place over the entire implant site, allowing for protrusion of the post through the mucosa.

The implant site is allowed to heal for approximately 6 to 8 weeks without any forces of function on it. A suitable prosthesis may then be constructed and attached to the post.

In experiments conducted to date, implants of the material described have been found to be quite permanent. They are non-resorbable and appear to be completely biologically compatible. In fact, it has been observed that a direct bone to to ceramic bond interface exists without the typical formation of encapsulating soft tissue which would permit some movement of the implant.

Experiments conducted to date seem to indicate that implants embodying the present invention generate a high success rate because of the combination of the particular type of material used and the shape or configuration of the implant. For example, implants have been constructed of the same shape and design as described above, but made of metal. Also implants of the material described above but in the same shape as the metal implant described were constructed. Both types were implanted and both types failed.

In another experiment, an implant embodying the present invention was implanted in the jaw of a monkey and has remained rigidly positioned for at least the last 30 months.

Thus it can be seen that this invention provides a prosthetic implant which is not rejected nor resorbed by the body and against which bone tissue firmly and directly interfaces. This has been found to be true in spite of one current theory which provides that ceramics tend to decompose in a solution of blood and water. In any case for whatever reason, whether it be the density or purity of the material or whatever, we have found no noticeable evidence of resorption.

It should become apparent and obvious from the above that other types of protrusions, such as a discontinuous series of protrusions, can be embossed on the side walls of an alumina implant embodying the present invention. The preferred configuration gives a maximal interface and mechanical interlock between the implant and the alveolar bone for supporting shear and lateral loads. The term "protrusion" is intended to encompass relatively macroscopic protrusions of a size similar to the protrusions illustrated. The term is not intended to encompass relatively microscopic structures such as pores or a rough surface.

Figure 5:
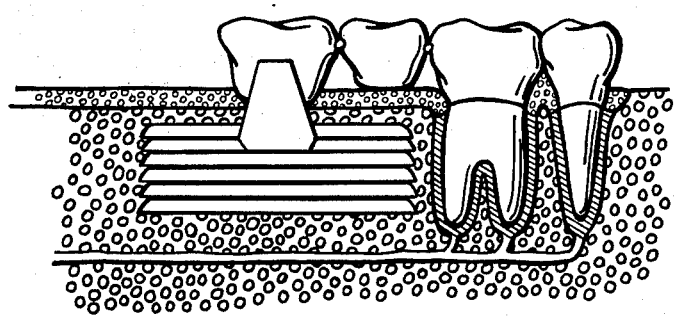
FIG. 5 is a view in vertical section illustrating the embodiment of FIG. 4 functionally positioned in healed alveolar bone and having prosthetic crown replacements mounted thereon.

With the implant illustrated in FIG. 5 the load bearing area is particularly maximized and spread over a large surface area. Although a single post or abutment is usually sufficient, two or more could be formed depending upon, among other things, the extent to which the dentist wished to attach the crowns to existing teeth such as by clasps for example.

It is to be understood that while the detailed drawings and specific examples given describe preferred embodiments of the invention they are for the purposes of illustration only, that the apparatus of the invention is not limited to the precise details and conditions disclosed and that various changes may be made therein without departing from the spirit of the invention which is defined by the following claims.

What is claimed is:

1. A dental, prosthetic, endostial implant comprising:
   a. a base formed of relatively high purity, high density, low porosity alumina, said base in an implanted operable position having opposite ends and having side walls integrally formed with outwardly projecting protrusions which include substantially flat horizontal surface areas facing in the direction of the implanted end, said surface areas being produced by a series of steps having undersurfaces whereby a significant area facing toward the implanted end is produced to transfer the axial loading over a greater area; and
   b. a post extending generally vertically from the other end of said base and contoured in a generally rounded, horizontal cross sectional configuration for attachment of at least one prosthetic crown.

2. An implant according to claim 1 wherein said post and base of said implant are integrally formed into a unitary body generally shaped like oppositely tapering truncated ellipsodial cones.

3. An implant according to claim 2 wherein the longitudinal axes of said post and base angularly intersect.

4. An implant according to claim 1 wherein said implant is integrally formed into a unitary body, and wherein said base is relatively elongated to a length greater than a single tooth to form an endostial blade type implant.

5. An implant according to claim 1 wherein said protrusions comprise a plurality of circumferentially extending continuous horizontal ridges integrally formed on the side walls of the base of said implant.

6. An implant according to claim 5 wherein said ridges have a sawtooth vertical cross sectional configuration.

7. An implant according to claim 1 said implant includes a trace amount of magnesia.

8. An implant according to claim 1 wherein said implant includes a trace amount of calcia.

9. An implant according to claim 1 wherein said implant includes a trace amount of silica.

10. An implant according to claim 1 wherein said base member includes trace amounts of at least two of the following: magnesia, calcia and silica.

11. An implant according to claim 1 wherein said implant is at least 99% pure alumina having a density at least as great as 93% of the theoretical maximum density.

12. An implant according to claim 11 wherein said density is at least as great as 97% of the theoretical maximum density.

13. An implant according to claim 1 wherein said implant is integrally formed into a unitary body, wherein said base is relatively elongated to form an endostial blade type implant and said protrusions are continuous horizontal ridges having a sawtooth vertical cross sectional configuration with alternate generally horizontal surface areas and oblique surfaces tapering outwardly away from said post and wherein said post has a truncated, ellipsoidally conical configuration tapering inwardly away from said base.

14. An implant according to claim 13 wherein said alumina implant includes a trace amount of magnesia.

15. An implant according to claim 13 wherein said implant includes a trace amount of calcia.

16. An implant according to claim 13 wherein said implant includes a trace amount of silica.

17. An implant according to claim 13 wherein said base member includes trace amounts of at least two of the following: magnesia, calcia and silica.

18. An implant according to claim 13 wherein said implant is at least 99% pure alumina having a density at least as great as 93% of the theoretical maximum density.

* * * * *

REEXAMINATION CERTIFICATE (64th)

United States Patent [19]
Driskell et al.

[11] B1 3,950,850
[45] Certificate Issued Mar. 22, 1983

[54] DENTAL PROSTHETIC IMPLANTS

[75] Inventors: Thomas D. Driskell; Alfred L. Heller, both of Worthington; Joseph F. Koenigs, Columbus, all of Ohio

[73] Assignee: Miter, Inc., Worthington, Ohio

Reexamination Request
No. 90/000,129, Dec. 21, 1981

Reexamination Certificate for:
Patent No.: 3,950,850
Issued: Apr. 20, 1976
Appl. No.: 445,567
Filed: Feb. 25, 1974

[51] Int. Cl.³ .............................................. A61C 8/00
[52] U.S. Cl. .................................................... 433/176
[58] Field of Search ................... 433/176, 173, 174, 175; 128/92 R

[56] References Cited

U.S. PATENT DOCUMENTS

| | | |
|---|---|---|
| 2,274,067 | 2/1942 | Jeffrey. |
| 2,857,670 | 10/1958 | Kiernan. |
| 3,465,441 | 9/1969 | Linkow. |
| 3,717,932 | 2/1973 | Brainin. |
| 3,729,825 | 5/1973 | Linkow et al. |
| 3,797,113 | 3/1974 | Brainin. |
| 3,827,145 | 8/1974 | Richards. |

FOREIGN PATENT DOCUMENTS

10837659  9/1967  United Kingdom.

OTHER PUBLICATIONS

Driskell, Thomas D. et al., "Surgical Tooth Implants, Combat and Field", Report No. 1, July, 1971, Contract No. DADA-69-C-9181.

Driskell, Thomas D. et al., "Surgical Tooth Implants, Combat and Field", Report No. 2, August 3, 1972, Contract No. DADA-69-C-9181.

*Primary Examiner*—Robert Peshock

[57] ABSTRACT

A prosthetic dental implant which is surgically implantable in the maxillary and mandibular alveolar bones, providing a support base with a protruding post to which one or more prosthetic crown replacements are to be mounted. The implant is a high purity, high density, low porosity unitary alumina body having a serrated base. Its integral top is formed to provide an upwardly extending post with a truncated ellipsodially conical configuration for the attachment of a prosthetic tooth crown. The serrated side walls of the base are formed with outwardly projecting protrusions. These protrusions have a serrated or saw toothed cross sectional configuration with alternating horizontal surfaces and downwardly and outwardly tapering oblique surfaces.

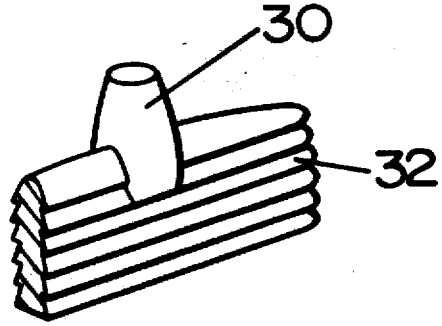

REEXAMINATION CERTIFICATE ISSUED UNDER 35 U.S.C. 307.

THE PATENT IS HEREBY AMENDED AS INDICATED BELOW.

Matter enclosed in heavy brackets appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended:

1. A dental, prosthetic, endostial implant comprising:
   a. a base formed of relatively high purity, high density, low porosity alumina, said base in an implanted operable position having opposite ends and having side walls integrally formed with *continuous* outwardly projecting protrusions which include *alternating* substantially flat horizontal surface areas facing in the direction of the implanted end *and downwardly and outwardly tapering oblique surface areas connecting therebetween for the purpose of optimizing the stress-bearing area of the bone-to-implant interfact* [, said surface areas being produced by a series of steps having undersurfaces whereby a significant area facing toward the implanted end is produced] to *effectively* transfer the axial *and lateral* loading over a greater area; and
   b. a post extending generally vertically from the other end of said base and contoured in a generally rounded, horizontal cross sectional configuration for attachment of at least one prosthetic crown.

Claims 2-18, dependent on amended claims, are determined to be patentable.

* * * * *